US008288426B2

(12) United States Patent
Hungenberg et al.

(10) Patent No.: US 8,288,426 B2
(45) Date of Patent: Oct. 16, 2012

(54) PESTICIDAL COMPOSITION COMPRISING FENAMIDONE AND AN INSECTICIDE COMPOUND

(75) Inventors: Heike Hungenberg, Langenfeld (DE); Wolfgang Thielert, Odenthal (DE); Koen Van Den Eynde, Merchtem (BE)

(73) Assignee: Bayer CropScience AG, Monheim (DE)

( * ) Notice: Subject to any disclaimer, the term of this patent is extended or adjusted under 35 U.S.C. 154(b) by 546 days.

(21) Appl. No.: 12/520,588

(22) PCT Filed: Dec. 21, 2007

(86) PCT No.: PCT/EP2007/064421
§ 371 (c)(1),
(2), (4) Date: Jun. 22, 2009

(87) PCT Pub. No.: WO2008/077922
PCT Pub. Date: Jul. 3, 2008

(65) Prior Publication Data
US 2010/0029776 A1  Feb. 4, 2010

(30) Foreign Application Priority Data

Dec. 22, 2006  (EP) .................................... 06127142

(51) Int. Cl.
*A01N 43/50* (2006.01)
*A01N 51/00* (2006.01)
*A01N 47/40* (2006.01)
*A01N 43/653* (2006.01)
*A01N 55/02* (2006.01)
*A01N 37/18* (2006.01)
*A01P 3/00* (2006.01)
*A01P 7/04* (2006.01)

(52) U.S. Cl. .............. 514/398; 514/27; 514/28; 514/30; 514/141; 514/229.2; 514/237.5; 514/266.23; 514/352; 514/367; 514/380; 514/383; 514/384; 514/386; 514/406; 514/422; 514/433; 514/478; 514/479; 514/483; 514/491; 514/492; 514/494; 514/525; 514/537; 514/539; 514/594; 514/622; 424/605

(58) Field of Classification Search .................. 514/28, 514/30, 398, 539, 27, 141, 229.2, 237.5, 514/266.23, 352, 367, 380, 383, 384, 386, 514/406, 422, 433, 478, 479, 483, 491, 492, 514/494, 525, 537, 594, 622
See application file for complete search history.

(56) References Cited

U.S. PATENT DOCUMENTS

| 4,761,373 A | 8/1988 | Anderson et al. |
|---|---|---|
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,824,790 A | 10/1998 | Keeling et al. |
| 5,840,946 A | 11/1998 | Wong et al. |
| 5,859,333 A | 1/1999 | Keeling et al. |
| 5,866,782 A | 2/1999 | Iwabuchi et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |
| 5,969,169 A | 10/1999 | Fan |
| 6,013,861 A | 1/2000 | Bird et al. |
| 6,028,249 A | 2/2000 | Rober et al. |
| 6,057,494 A | 5/2000 | Koops et al. |
| 6,063,947 A | 5/2000 | DeBonte et al. |
| 6,066,782 A | 5/2000 | Kossmann et al. |

(Continued)

FOREIGN PATENT DOCUMENTS

DE  10310906  9/2004

(Continued)

OTHER PUBLICATIONS

Latorse, M.P. et al., "Sensitivity base line and resistance monitoring on *Plasmopara viticola* and *Phytophthora infestans*," Pflanzenschutz-Nachrichten Bayer, vol. 56(3), pp. 511-522 (2003).*
Mercer, R.T. et al., "Fungicidal properties of the active ingredient—fenamidone," Pflanzenschutz-Nachrichten Bayer, vol. 56(3), pp. 465-476 (2003).*
Farm Chemicals Handbook '98, Meister Publishing Co., Willoughby, Ohio, vol. 84, pp. C5 and C196 (1998).*
Webster's New World Dictionary, second college ed., The World Publishing Co., New York, 1972, p. 1127.*
Colby, "Calculating Synergistic and Antagonistic Responses of Herbicide Combinations," Weeds, (1967), 15, pp. 20-22.

(Continued)

*Primary Examiner* — John Pak
(74) *Attorney, Agent, or Firm* — Baker Donelson Bearman Caldwell & Berkowitz, PC

(57) ABSTRACT

A composition comprising fenamidone (a) and an insecticide compound (b) in a (a)/(b) weight ratio of from 1/1000 to 1000/1.
A composition further comprising an additional fungicidal compound.
A method for preventively or curatively combating the pests and diseases of crops by using this composition.

20 Claims, No Drawings

U.S. PATENT DOCUMENTS

| | | | |
|---|---|---|---|
| 6,103,893 A | 8/2000 | Cooke et al. | |
| 6,117,665 A | 9/2000 | Kossmann et al. | |
| 6,130,367 A | 10/2000 | Kossmann et al. | |
| 6,162,966 A | 12/2000 | Kossmann et al. | |
| 6,169,190 B1 | 1/2001 | Lanuza et al. | |
| 6,207,880 B1 | 3/2001 | Kossmann et al. | |
| 6,211,436 B1 | 4/2001 | Kossmann et al. | |
| 6,215,042 B1 | 4/2001 | Willmitzer et al. | |
| 6,229,072 B1 | 5/2001 | Burns et al. | |
| 6,232,529 B1 | 5/2001 | Singletary et al. | |
| 6,245,968 B1 | 6/2001 | Boudec et al. | |
| 6,255,561 B1 | 7/2001 | Kossmann et al. | |
| 6,255,563 B1 | 7/2001 | Emmermann et al. | |
| 6,265,635 B1 | 7/2001 | Kossmann et al. | |
| 6,268,549 B1 | 7/2001 | Sailland et al. | |
| 6,270,828 B1 | 8/2001 | DeBonte et al. | |
| 6,284,479 B1 | 9/2001 | Nichols | |
| 6,307,124 B1 | 10/2001 | Kossmann et al. | |
| 6,307,125 B1 | 10/2001 | Block et al. | |
| 6,323,392 B1 | 11/2001 | Charne | |
| 6,353,154 B1 | 3/2002 | Kossmann et al. | |
| 6,462,256 B1 | 10/2002 | Abel et al. | |
| 6,472,588 B1 | 10/2002 | Haigler et al. | |
| 6,495,740 B1 | 12/2002 | Arioli et al. | |
| 6,515,203 B1 | 2/2003 | Heyer et al. | |
| 6,559,356 B1 | 5/2003 | Heyer et al. | |
| 6,566,585 B1 | 5/2003 | Quanz | |
| 6,566,587 B1 | 5/2003 | Lebrun et al. | |
| 6,570,065 B1 | 5/2003 | Kossmann et al. | |
| 6,590,141 B1 | 7/2003 | Frohberg | |
| 6,596,928 B1 | 7/2003 | Landschutze | |
| 6,635,756 B1 | 10/2003 | Jobling et al. | |
| 6,699,694 B1 | 3/2004 | Buttcher et al. | |
| 6,734,341 B2 | 5/2004 | Singletary et al. | |
| 6,791,010 B1 | 9/2004 | Frohberg | |
| 6,794,558 B1 | 9/2004 | Frohberg | |
| 6,812,010 B1 | 11/2004 | Derose et al. | |
| 6,822,144 B1 | 11/2004 | Zhao et al. | |
| 6,825,342 B1 | 11/2004 | Cooke et al. | |
| 6,890,732 B1 | 5/2005 | Loerz et al. | |
| 6,891,088 B1 | 5/2005 | Neuhaus et al. | |
| 6,940,001 B1 | 9/2005 | Landschutze | |
| 6,951,969 B1 | 10/2005 | Loerz et al. | |
| 6,956,148 B1 | 10/2005 | Jobling et al. | |
| 7,112,665 B1 | 9/2006 | Leemans et al. | |
| 7,186,898 B1 | 3/2007 | Kossmann et al. | |
| 2002/0031826 A1 | 3/2002 | Nichols | |
| 2004/0073966 A1 | 4/2004 | Zink et al. | |
| 2004/0110443 A1 | 6/2004 | Pelham, Sr. | |
| 2005/0257283 A1 | 11/2005 | Matringe et al. | |
| 2006/0130181 A1 | 6/2006 | Hoehne et al. | |
| 2006/0150278 A1 | 7/2006 | Frohberg et al. | |
| 2006/0162021 A1 | 7/2006 | Hofvander et al. | |
| 2006/0168690 A1 | 7/2006 | Shibatani et al. | |
| 2006/0253929 A1 | 11/2006 | Frohberg | |
| 2007/0011777 A1 | 1/2007 | Frohberg | |
| 2007/0163003 A1 | 7/2007 | Frohberg et al. | |
| 2007/0163004 A1 | 7/2007 | Frohberg et al. | |
| 2007/0174932 A1 | 7/2007 | Uwer et al. | |
| 2007/0300322 A1 | 12/2007 | De Block et al. | |
| 2008/0022421 A1 | 1/2008 | Frohberg et al. | |
| 2008/0221167 A1 | 9/2008 | Fischer et al. | |
| 2008/0248188 A1 | 10/2008 | Schewe et al. | |
| 2008/0250533 A1 | 10/2008 | Frohberg | |
| 2008/0251225 A1 | 10/2008 | Landschuetze et al. | |
| 2008/0262044 A1 | 10/2008 | Dutton et al. | |
| 2008/0276336 A1 | 11/2008 | Frohberg et al. | |
| 2009/0013431 A1 | 1/2009 | Van Thournout et al. | |
| 2009/0028837 A1 | 1/2009 | De Block et al. | |
| 2009/0064371 A1 | 3/2009 | Metzlaff et al. | |
| 2009/0064372 A1 | 3/2009 | Kok-Jacon et al. | |
| 2009/0105469 A1 | 4/2009 | Soyka et al. | |
| 2009/0106863 A1 | 4/2009 | Frohberg et al. | |
| 2009/0151016 A1 | 6/2009 | Frohberg et al. | |
| 2009/0151021 A1 | 6/2009 | Bots et al. | |
| 2009/0199311 A1 | 8/2009 | Frohberg et al. | |
| 2009/0205069 A1 | 8/2009 | Babiychuk et al. | |
| 2009/0238798 A1 | 9/2009 | Bogdanova et al. | |

FOREIGN PATENT DOCUMENTS

| | | |
|---|---|---|
| EP | 0629616 | 12/1994 |
| JP | 2006304779 | 9/2006 |
| WO | 89/10396 A1 | 11/1989 |
| WO | 91/02069 A1 | 2/1991 |
| WO | 92/05251 A1 | 4/1992 |
| WO | 94/09144 A1 | 4/1994 |
| WO | 94/11520 A2 | 5/1994 |
| WO | 94/21795 A1 | 9/1994 |
| WO | 95/35026 A1 | 12/1995 |
| WO | 96/01904 A1 | 1/1996 |
| WO | 96/33270 A1 | 10/1996 |
| WO | 96/37494 A1 | 11/1996 |
| WO | 97/20936 A1 | 5/1997 |
| WO | 97/41218 A1 | 11/1997 |
| WO | 97/47806 A1 | 12/1997 |
| WO | 97/47807 A1 | 12/1997 |
| WO | 97/47808 A1 | 12/1997 |
| WO | 98/25923 A1 | 6/1998 |
| WO | 98/27806 A1 | 7/1998 |
| WO | 99/12950 A2 | 3/1999 |
| WO | 99/24585 A1 | 5/1999 |
| WO | 9927788 | 6/1999 |
| WO | 99/53072 A1 | 10/1999 |
| WO | 99/57965 A1 | 11/1999 |
| WO | 00/11192 A2 | 3/2000 |
| WO | 00/14249 A1 | 3/2000 |
| WO | 00/28052 A2 | 5/2000 |
| WO | 00/66746 A1 | 11/2000 |
| WO | 00/66747 A1 | 11/2000 |
| WO | 01/14569 A2 | 3/2001 |
| WO | 01/19975 A2 | 3/2001 |
| WO | 01/24615 A1 | 4/2001 |
| WO | 01/65922 A2 | 9/2001 |
| WO | 01/66704 A2 | 9/2001 |
| WO | 01/98509 A2 | 12/2001 |
| WO | 02/26995 A1 | 4/2002 |
| WO | 02/36792 A2 | 5/2002 |
| WO | 02/45485 A1 | 6/2002 |
| WO | 02/079410 A2 | 10/2002 |
| WO | 03/013226 A2 | 2/2003 |
| WO | 03/024222 * | 3/2003 |
| WO | 03/033540 A2 | 4/2003 |
| WO | 03/092360 A2 | 11/2003 |
| WO | 2004/090140 A2 | 10/2004 |
| WO | 2004/106529 A2 | 12/2004 |
| WO | 2005/002324 A2 | 1/2005 |
| WO | 2005/002359 A2 | 1/2005 |
| WO | 95/04826 A1 | 2/2005 |
| WO | 2005/012515 A2 | 2/2005 |
| WO | 2005/017157 A1 | 2/2005 |
| WO | 2005/020673 A1 | 3/2005 |
| WO | 2005/093093 A2 | 10/2005 |
| WO | 2005094155 | 10/2005 |
| WO | 2006/007373 A2 | 1/2006 |
| WO | 2006/015376 A2 | 2/2006 |
| WO | 2006/018319 A1 | 2/2006 |
| WO | 2006/021972 A1 | 3/2006 |
| WO | 2006/024351 A1 | 3/2006 |
| WO | 2006/032538 A1 | 3/2006 |
| WO | 2006/060634 A2 | 6/2006 |
| WO | 2006/072603 A2 | 7/2006 |
| WO | 2006/108702 A1 | 10/2006 |
| WO | 2007/024782 A2 | 3/2007 |
| WO | 2007/107326 A1 | 9/2007 |
| WO | 2007101547 | 9/2007 |
| WO | 2008/017518 A1 | 2/2008 |
| WO | 2008/080630 A1 | 7/2008 |
| WO | 2008/080631 A1 | 7/2008 |
| WO | 2008/090008 A1 | 7/2008 |

OTHER PUBLICATIONS

Comai et al., "An Altered aroA Gene Product Confers Resistance to the Herbicide Glyphosate," Science (1983), vol. 221, pp. 370-371.

Barry et al., "Inhibitors of Amino Acid Biosynthesis: Strategies for Imparting Glyphosate Tolerance to Crop Plants," Curr. Topics Plant Physiol. (1992), vol. 7, pp. 139-145.

Shah et al., "Engineering Herbicide Tolerance in Transgenic Plants," Science (1986), vol. 233, pp. 478-481.

Gasser et al., "Structure, Expression, and Evolution of the 5-Enolpyruvylshikimate-3-phosphate Synthase Genes of Petunia and Tomato," J. Biol. Chem (1988), vol. 263, pp. 4280-4289.

Moellenbeck et al., "Insecticidal proteins from *Bacillus thuringiensis* protect corn from corn rootworms," Nat. Biotechnol. (2001), vol. 19, pp. 668-672.

Schnepf et al., "Chaacterization of Cry34/Cry35 Binary Insecticidal Proteins from Diverse *Bacillus thuringiensis* Strain Collections," Applied Environm. Microbiol. (2006), vol. 71, pp. 1765-1774.

International Search Report dated Mar. 25, 2008 (8 pages).

* cited by examiner

PESTICIDAL COMPOSITION COMPRISING FENAMIDONE AND AN INSECTICIDE COMPOUND

CROSS REFERENCE TO RELATED APPLICATIONS

This application is a §371 National Stage Application of PCT/EP2007/064421, filed Dec, 21, 2007 which claims priority to EP 06127142.5 filed Dec. 22, 2006.

BACKGROUND OF THE INVENTION

1. Field of the Invention

The present invention relates to novel pesticidal compositions comprising a pyridylethylbenzamide derivative and an insecticide compound. The present invention also relates to a method of combating or controlling pests by applying at a locus infested or liable to be infested such a composition.

2. Description of Related Art

European patent application EP-629616 discloses numerous 2-imidazolin-5-one derivatives including fenamidone, and their use as fungicide. The possibility of combining one or more of these 2-imidazolin-5-one derivatives with known fungicidal products to develop a fungicidal activity is disclosed. No mention is made of a possible association of fenamidone with an insecticide active ingredient.

International patent application WO-99/027788 discloses compositions comprising 2-imidazolin-5-one derivatives according to the present invention in mixture with other fungicide active ingredients and their use as fungicide. No mention is made of mixtures comprising fenamidone with an insecticide active ingredient.

In international patent application WO-2007/101547 there are generically disclosed numerous mixtures of some phthalamide insecticide compounds with known fungicide substances. The association of these insecticide compounds with fenamidone has not been specifically disclosed nor has been subject to any experimentation. Such an association does not form part of the present invention.

It is always of high-interest in agriculture to use novel pesticidal mixtures showing a broader scope of activity and a fungicide or insecticide synergistic effect in order notably to avoid or to control the development of resistant strains to the active ingredients or to the mixtures of known active ingredients used by the farmer while minimising the doses of chemical products spread in the environment and reducing the cost of the treatment.

SUMMARY OF THE INVENTION

We have now found some novel pesticidal compositions which possess the above mentioned characteristics.

Accordingly, the present invention relates to a composition comprising
a) fenamidone; and
b) an insecticide compound;
in a (a)/(b) weight ratio of from 1/1000 to 1000/1;
provided that insecticide B compound is different from compounds of general formula (II)

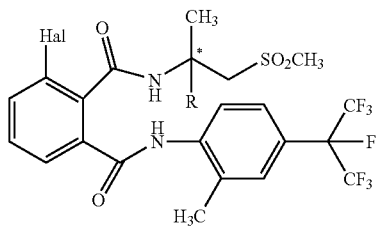

wherein
Hal represents a chlorine atom, a bromine atom or a iodine atom;
R represents hydrogen or methyl and * may represent a carbon atom in R- or S-configuration.

DETAILED DESCRIPTION OF A PREFERRED EMBODIMENT

The composition according to the present invention provides a synergistic effect. This synergistic effect allows a reduction of the chemical substances spread into the environment and a reduction of the cost of the pesticidal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x * y}{100}$$

in which E represents the expected percentage of inhibition of the pest for the combination of the two pesticides at defined doses (for example equal to x and y respectively), x is the percentage of inhibition observed for the pest by the compound (a) at a defined dose (equal to x), y is the percentage of inhibition observed for the pest by the compound (b) at a defined dose (equal to y). When the percentage of inhibition observed for the combination is greater than E, there is a synergistic effect.

The latter article also mentions the formula:

$$E = x + y + z - \frac{x * y * z}{100}$$

in which E represents the expected percentage of inhibition of the pest for the combination of the three pesticides at defined doses (for example equal to x, y and z respectively), x is the percentage of inhibition observed for the pest by the compound (a) at a defined dose (equal to x), y is the percentage of inhibition observed for the pest by the compound (b) at a defined dose (equal to y) and z is the percentage of inhibition observed for the pest by the compound (c) at a defined dose (equal to z). When the percentage of inhibition observed for the combination is greater than E, there is a synergistic effect.

The composition according to the present invention comprises an insecticide compound (b). Suitable insecticide includes:

The composition according to the present invention comprises an insecticide compound (b). Suitable insecticide are chosen in the following groups:
b1) acetylcholine receptor agonists/antagonists such as chloronicotinyls/neonicotinoids, nicotine, bensultap or cartap. Suitable examples of chloronicotinyls/neonicotinoids include acetamiprid, clothianidin, dinotefuran, imidacloprid, nitenpyram, nithiazine, thiacloprid, thiamethoxam, imidaclothiz and (2E)-1-[(2-chloro-1,3-thiazol-5-yl)methyl]-3,5-dimethyl-N-nitro-1,3,5-triazinan-2-imine;

b2) acetylcholinesterase (AChE) inhibitors such as carbamates and organophosphates. Suitable examples of carbamates include alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC and xylylcarb. Suitable examples of organophosphates include acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-5-methyl, demeton-5-methylsulphon, dialifos, diazinon, dichlofenthion, dichlorvos/DDVP, dicrotophos, di-methoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon and vamidothion;

b3) sodium channel modulators/voltage-gated sodium channel blockers such as pyrethroids and oxadiazines. Suitable examples of pyrethroids include acrinathrin, allethrin (d-cis-trans, d-trans), beta-cyfluthrin, bifenthrin, bioallethrin, bioallethrin-5-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (IR-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901 and pyrethrins (pyrethrum). Suitable example of oxadiazines includes indoxacarb;

b4) acetylcholine receptor modulators such as spinosyns. Suitable example of spinosyns includes spinosad;

b5) GABA-gated chloride channel antagonists such as cyclodiene organochlorines and fiproles. Suitable examples of cyclodiene organochlorines include camphechlor, chlordane, endosulfan, gamma-HCH, HCH, heptachlor, lindane and methoxychlor. Suitable examples of fiproles include acetoprole, ethiprole, fipronil and vaniliprole;

b6) chloride channel activators such as mectins. Suitable examples of mectins include abamectin, avermectin, emamectin, emamectin-benzoate, ivennectin, lepimectin, milbemectin and milbemycin;

b7) juvenile hormone mimetics such as diofenolan, epofenonane, fenoxycarb, hydroprene, kinoprene, methoprene, pyriproxifen, triprene;

b8) ecdysone agonists/disruptors such as diacylhydrazines. Suitable examples of diacylhydrazines include chromafenozide, halofenozide, methoxyfenozide and tebufenozide;

b9) inhibitors of chitinbiosynthesis such as benzoylureas, buprofezin and cyromazine. Suitable examples of benzoylureas include bistrifluron, chlofluazuron, diflubenzuron, fluazuron, flucycloxuron, flufenoxuron, hexaflumuron, lufenuron, novaluron, noviflumuron, penfluoron, teflubenzuron and triflumuron;

b10) inhibitors of oxidative phosphorylation, ATP disruptors such as organotins and diafenthiuron. Suitable examples of organotins include azocyclotin, cyhexatin and fenbutatin oxide;

b11) decouplers of oxidative phosphorylation by disruption of the H proton gradient such as pyrroles and dinitrophenols. Suitable example of pyrroles includes chlorfenapyr. Suitable examples of dinitrophenols include binapacyrl, dinobuton, dinocap and DNOC;

b12) site I electron transport inhibitors such as METIs, hydramethylnone and dicofol. Suitable examples of METIs include fenazaquin, fenpyroximate, pyrimidifen, pyridaben, tebufenpyrad, tolfenpyrad;

b13) site II electron transport inhibitors such as rotenone;

b14) site III electron transport inhibitors such as acequinocyl and fluacrypyrim;

b15) microbial disrupters of the intestinal membrane of insects such as *Bacillus thuringiensis* strains;

b16) inhibitors of lipid synthesis such as tetronic acids and tetramic acids. Suitable examples of tetronic acids include spirodiclofen, spiromesifen and spirotetramat. Suitable example of tetramic acids includes cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester (CAS Reg. No.: 382608-10-8)

b17) carboxamides such as flonicamid;

b18) octopaminergic agonists such as amitraz;

b19) inhibitors of the magnesium-stimulated ATPase such as propargite;

b20) ryanodin receptor agonists such as phthalamides or rynaxapyr. Suitable example of phthalamides includes $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (i.e. flubendiamide, CAS reg. No.: 272451-65-7);

b21) nereistoxin analogues such as thiocyclam hydrogen oxalate andthiosultap-sodium;

b22) biologics, hormones or pheromones such as azadirachtin, *Bacillus* spec., *Beauveria* spec., *codlemone*, *Metarrhizium* spec., *Paecilomyces* spec., *thuringiensis* and *Verticillium* spec;

b23) active compounds having unknown or non-specified mechanisms of action such as fumigants, selective feeding inhibitors, mite growth inhibitors, amidoflumet; benclothiaz, benzoximate, bifenazate, bromopropylate, buprofezin, chinomethioat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS reg. No. 185982-80-3) and the corresponding 3-endo isomer (CAS reg. No. 185984-60-5) (cf. WO 96/37494, WO 98/25923), and also preparations comprising insecticidal effective plant extracts, nematodes, fungi or viruses. Suitable examples of fumigants include aluminium phosphide, methyl bromide and sulphuryl fluoride. Suitable examples of selective feeding inhibitors include cryolite, flonicamid and pymetrozine. Suitable examples of mite growth inhibitors include clofentezine, etoxazole and hexythiazox.

Preferably, the insecticide compound (b) is chosen as being abamectin, acephate, acetamiprid, acrinathrin, aldicarb, alpha-cypermethrin, beta-cyfluthrin, bifenthrin, carbaryl, carbofuran, chlorfenapyr, chlorfluazuron, chlorpyrifos-E, clothianidin, cyfluthrin, cypermethrin, cyromazine, deltamethrin, diflubenzuron, dinotefuran, emamectin benzoate, ethiprole, fenpyroximate, fipronil, flonicamid, flubendiamide, flufenoxuron, gamma-cyhalothrin, hexaflumuron, imidacloprid, indoxacarb, L-cyhalothrin, lepimectin, lufenuron, methamidophos, methiocarb, methomyl, methoxyfenozide, milbemycin, nitenpyram, novaluron, profenofos, pymetrozine, rynaxapyr, spinosad, spirodiclofen, spiromesifen, spirotetramate, tebufenozide, tebufenozide, tebufenpyrad, tebufenpyrad, tebupirimphos, teflubenzuron, tefluthrin, thiacloprid, thiamethoxam, thiodicarb, triazophos triflumuron, imidaclothiz and (2E)-1-[(2-chloro-1,3-thiazol-5-yl)methyl]-3,5-dimethyl-N-nitro-1,3,5-triazinan-2-imine. More preferably, the insecticide compound (b) is chosen as being abamectin, acetamiprid, aldicarb, beta-cyfluthrin, carbofuran, chlorpyrifos-E, clothianidin, cypermethrin, cyromazine, deltamethrin, diflubenzuron, emamectin benzoate, ethiprole, fipronil, gamma-cyhalothrin, imidacloprid, L-cyhalothrin, lufenuron, methiocarb, methoxyfenozide, pymetrozine, rynaxapyr, spinosad, spirodiclofen, spiromesifen, spirotetramate, tebufenozide, tebufenpyrad, tefluthrin, thiacloprid, thiamethoxam, thiodicarb, triflumuron, imidaclothiz and (2E)-1-[(2-chloro-1,3-thiazol-5-yl)methyl]-3,5-dimethyl-N-nitro-1,3,5-triazinan-2-imine. Even more preferably, the insecticide compound (b) is chosen as being abamectin, aldicarb, beta-cyfluthrin, chlorpyrifos-E, clothianidin, cyromazine, deltamethrin, diflubenzuron, emamectin benzoate, fipronil, gamma-cyhalothrin, imidacloprid, L-cyhalothrin, methiocarb, pymetrozine, rynaxapyr, spinosad, spirodiclofen, spiromesifen, spirotetramate, tebufenozide, tebufenpyrad, tefluthrin, thiamethoxam, thiodicarb, imidaclothiz, (2E)-1-[(2-chloro-1,3-thiazol-5-yl)methyl]-3,5-dimethyl-N-nitro-1,3,5-triazinan-2-imine.

Non limitative examples of suitable mixtures according to the present invention may include mixtures of fenamidone with abamectin, fenamidone with acephate, fenamidone with acetamiprid, fenamidone with acrinathrin, fenamidone with aldicarb, fenamidone with alpha-cypermethrin, fenamidone with beta-cyfluthrin, fenamidone with bifenthrin, fenamidone with carbaryl, fenamidone with carbofuran, fenamidone with chlorfenapyr, fenamidone with chlorfluazuron, fenamidone with chlorpyrifos-E, fenamidone with clothianidin, fenamidone with cyfluthrin, fenamidone with cypermethrin, fenamidone with cyromazine, fenamidone with deltamethrin, fenamidone with diflubenzuron, fenamidone with dinotefuran, fenamidone with emamectin benzoate, fenamidone with ethiprole, fenamidone with fenpyroximate, fenamidone with fipronil, fenamidone with flonicamid, fenamidone with flubendiamide, fenamidone with flufenoxuron, fenamidone with gamma-cyhalothrin, fenamidone with hexaflumuron, fenamidone with imidacloprid, fenamidone with indoxacarb, fenamidone with L-cyhalothrin, fenamidone with lepimectin, fenamidone with lufenuron, fenamidone with methamidophos, fenamidone with methiocarb, fenamidone with methomyl, fenamidone with methoxyfenozide, fenamidone with milbemycin, fenamidone with nitenpyram, fenamidone with novaluron, fenamidone with profenofos, fenamidone with pymetrozine, fenamidone with rynaxapyr, fenamidone with spinosad, fenamidone with spirodiclofen, fenamidone with spiromesifen, fenamidone with spirotetramate, fenamidone with tebufenozide, fenamidone with tebufenozide, fenamidone with tebufenpyrad, fenamidone with tebufenpyrad, fenamidone with tebupirimphos, fenamidone with teflubenzuron, fenamidone with tefluthrin, fenamidone with thiacloprid, fenamidone with thiamethoxam, fenamidone with thiodicarb, fenamidone with triazophos, fenamidone with triflumuron, fenamidone with imidaclothiz and fenamidone with (2E)-1-[(2-chloro-1,3-thiazol-5-yl)methyl]-3,5-dimethyl-N-nitro-1,3,5-triazinan-2-imine.

The composition according to the present invention comprises a compound of general formula (I) (a) and an insecticide compound (b) in a synergistically effective weight ratio of a:b of from 1/1000 to 1000/1. Preferably, (a)/(b) weight ratio is of from 1/125 to 125/1. Even more preferably, (a)/(b) weight ratio is of from 1/25 to 25/1.

Furthermore in the combinations according to the invention the compounds A and B are present in a synergistically effective weight ratio of A:B in a range of 100:1 to 1:50, 100:1 to 1:20, 50:1 to 1:100, 50:1 to 1:20, 20:1 to 1:100, 20:1 to 1:50. Further ratios of A:B which can be used according to the present invention with increasing preference in the order given are: 95:1 to 1:95, 95:1 to 1:90, 95:1 to 1:85, 95:1 to 1:80, 95:1 to 1:75, 95:1 to 1:70, 95:1 to 1:65, 95:1 to 1:60, 95:1 to 1:55, 95:1 to 1:50, 95:1 to 1:45, 95:1 to 1:40, 95:1 to 1:35, 95:1 to 1:30, 95:1 to 1:25, 95:1 to 1:20, 95:1 to 1:15, 95:1 to 1:10, 95:1 to 1:5, 95:1 to 1:4, 95:1 to 1:3, 95:1 to 1:2, 90:1 to 1:90, 90:1 to 1:95, 90:1 to 1:85, 90:1 to 1:80, 90:1 to 1:75, 90:1 to 1:70, 90:1 to 1:65, 90:1 to 1:60, 90:1 to 1:55, 90:1 to 1:50, 90:1 to 1:45, 90:1 to 1:40, 90:1 to 1:35, 90:1 to 1:30, 90:1 to 1:25, 90:1 to 1:20, 90:1 to 1:15, 90:1 to 1:10, 90:1 to 1:5, 90:1 to 1:4, 90:1 to 1:3, 90:1 to 1:2, 85:1 to 1:85, 85:1 to 1:95, 85:1 to 1:90, 85:1 to 1:80, 85:1 to 1:75, 85:1 to 1:70, 85:1 to 1:65, 85:1 to 1:60, 85:1 to 1:55, 85:1 to 1:50, 85:1 to 1:45, 85:1 to 1:40, 85:1 to 1:35, 85:1 to 1:30, 85:1 to 1:25, 85:1 to 1:20, 85:1 to 1:15, 85:1 to 1:10, 85:1 to 1:5, 85:1 to 1:4, 85:1 to 1:3, 85:1 to 1:2, 80:1 to 1:80, 80:1 to 1:95, 80:1 to 1:90, 80:1 to 1:85, 80:1 to 1:75, 80:1 to 1:70, 80:1 to 1:65, 80:1 to 1:60, 80:1 to 1:55, 80:1 to 1:50, 80:1 to 1:45, 80:1 to 1:40, 80:1 to 1:35, 80:1 to 1:30, 80:1 to 1:25, 80:1 to 1:20, 80:1 to 1:15, 80:1 to 1:10, 80:1 to 1:5, 80:1 to 1:4, 80:1 to 1:3, 80:1 to 1:2, 75:1 to 1:75, 75:1 to 1:95, 75:1 to 1:90, 75:1 to 1:85, 75:1 to 1:80, 75:1 to 1:70, 75:1 to 1:65, 75:1 to 1:60, 75:1 to 1:55, 75:1 to 1:50, 75:1 to 1:45, 75:1 to 1:40, 75:1 to 1:35, 75:1 to 1:30, 75:1 to 1:25, 75:1 to 1:20, 75:1 to 1:15, 75:1 to 1:10, 75:1 to 1:5, 75:1 to 1:4, 75:1 to 1:3, 75:1 to 1:2, 70:1 to 1:70, 70:1 to 1:95, 70:1 to 1:90, 70:1 to 1:85, 70:1 to 1:80, 70:1 to 1:75, 70:1 to 1:65, 70:1 to 1:60, 70:1 to 1:55, 70:1 to 1:50, 70:1 to 1:45, 70:1 to 1:40, 70:1 to 1:35, 70:1 to 1:30, 70:1 to 1:25, 70:1 to 1:20, 70:1 to 1:15, 70:1 to 1:10, 70:1 to 1:5, 70:1 to 1:4, 70:1 to 1:3, 70:1 to 1:2, 65:1 to 1:65, 65:1 to 1:95, 65:1 to 1:90, 65:1 to 1:85, 65:1 to 1:80, 65:1 to 1:75, 65:1 to 1:70, 65:1 to 1:60, 65:1 to 1:55, 65:1 to 1:50, 65:1 to 1:45, 65:1 to 1:40, 65:1 to 1:35, 65:1 to 1:30, 65:1 to 1:25, 65:1 to 1:20, 65:1 to 1:15, 65:1 to 1:10, 65:1 to 1:5, 65:1 to 1:4, 65:1 to 1:3, 65:1 to 1:2, 60:1 to 1:60, 60:1 to 1:95, 60:1 to 1:90, 60:1 to 1:85, 60:1 to 1:80, 60:1 to 1:75, 60:1 to 1:70, 60:1 to 1:65, 60:1 to 1:55, 60:1 to 1:50, 60:1 to 1:45, 60:1 to 1:40, 60:1 to 1:35, 60:1 to 1:30, 60:1 to 1:25, 60:1 to 1:20, 60:1 to 1:15, 60:1 to 1:10, 60:1 to 1:5, 60:1 to 1:4, 60:1 to 1:3, 60:1 to 1:2, 55:1 to 1:55, 55:1 to 1:95, 55:1 to 1:90, 55:1 to 1:85, 55:1 to 1:80, 55:1 to 1:75, 55:1 to 1:70, 55:1 to 1:65, 55:1 to 1:60, 55:1 to 1:50, 55:1 to 1:45, 55:1 to 1:40, 55:1 to 1:35, 55:1 to 1:30, 55:1 to 1:25, 55:1 to 1:20, 55:1 to 1:15, 55:1 to 1:10, 55:1 to 1:5, 55:1 to 1:4, 55:1 to 1:3, 55:1 to 1:2, 50:1 to 1:95, 50:1 to 1:90, 50:1 to 1:85, 50:1 to 1:80, 50:1 to 1:75, 50:1 to 1:70, 50:1 to 1:65, 50:1 to 1:60, 50:1 to 1:55, 50:1 to 1:45, 50:1 to 1:40, 50:1 to 1:35, 50:1 to 1:30, 50:1 to 1:25, 50:1 to 1:20, 50:1 to 1:15, 50:1 to 1:10, 50:1 to 1:5, 50:1 to 1:4, 50:1 to 1:3, 50:1 to 1:2, 45:1 to 1:45, 45:1 to 1:95, 45:1 to 1:90, 45:1 to 1:85, 45:1 to 1:80, 45:1 to 1:75, 45:1 to 1:70, 45:1 to 1:65, 45:1 to 1:60, 45:1 to 1:55, 45:1 to 1:50, 45:1 to 1:40, 45:1 to 1:35, 45:1 to 1:30, 45:1 to 1:25, 45:1 to 1:20, 45:1 to 1:15, 45:1 to 1:10, 45:1 to 1:5, 45:1 to 1:4, 45:1 to 1:3, 45:1 to 1:2, 40:1 to 1:40, 40:1 to 1:95, 40:1 to 1:90, 40:1 to 1:85, 40:1 to 1:80, 40:1 to 1:75, 40:1 to 1:70, 40:1 to 1:65, 40:1 to 1:60, 40:1 to 1:55, 40:1 to 1:50, 40:1 to 1:45, 40:1 to 1:35, 40:1 to 1:30, 40:1 to 1:25, 40:1 to 1:20, 40:1 to 1:15, 40:1 to 1:10, 40:1 to 1:5, 40:1 to 1:4, 40:1 to 1:3, 40:1 to 1:2, 35:1 to 1:35, 35:1 to 1:95, 35:1 to 1:90, 35:1 to 1:85, 35:1 to 1:80, 35:1 to 1:75, 35:1 to 1:70, 35:1 to 1:65, 35:1 to 1:60, 35:1 to 1:55, 35:1 to 1:50, 35:1 to 1:45, 35:1 to 1:40, 35:1 to 1:30, 35:1 to 1:25, 35:1 to 1:20, 35:1 to 1:15, 35:1 to 1:10, 35:1 to 1:5, 35:1 to 1:4, 35:1 to 1:3, 35:1 to 1:2, 30:1 to 1:30, 30:1 to 1:95, 30:1 to 1:90, 30:1 to 1:85, 30:1 to 1:80, 30:1 to 1:75, 30:1 to 1:70, 30:1 to 1:65, 30:1 to 1:60, 30:1 to 1:55, 30:1 to 1:50, 30:1 to 1:45, 30:1 to 1:40, 30:1 to 1:35, 30:1 to 1:25, 30:1 to 1:20, 30:1 to 1:15, 30:1 to 1:10, 30:1 to 1:5, 30:1 to 1:4, 30:1 to 1:3, 30:1 to 1:2, 25:1 to 1:25, 25:1 to 1:95, 25:1 to 1:90, 25:1 to 1:85, 25:1 to 1:80, 25:1 to 1:75, 25:1 to 1:70, 25:1 to 1:65, 25:1 to 1:60, 25:1 to 1:55, 25:1 to 1:50, 25:1 to 1:45, 25:1 to 1:40, 25:1 to 1:35, 25:1 to 1:30, 25:1 to 1:20, 25:1 to 1:15, 25:1 to 1:10, 25:1 to 1:5, 25:1 to 1:4, 25:1 to 1:3, 25:1 to 1:2, 20:1 to 1:95, 20:1 to 1:90, 20:1 to 1:85, 20:1 to 1:80, 20:1 to 1:75, 20:1 to 1:70, 20:1 to 1:65, 20:1 to 1:60, 20:1 to 1:55, 20:1 to 1:50, 20:1 to 1:45, 20:1 to 1:40, 20:1 to 1:35, 20:1 to 1:30, 20:1 to 1:25, 20:1 to 1:15, 20:1 to 1:10, 20:1 to 1:5, 20:1 to 1:4, 20:1 to 1:3, 20:1 to 1:2, 15:1 to 1:15, 15:1 to 1:95, 15:1 to 1:90, 15:1 to 1:85, 15:1 to 1:80, 15:1 to 1:75, 15:1 to 1:70, 15:1 to 1:65, 15:1 to 1:60, 15:1 to 1:55, 15:1 to 1:50, 15:1 to 1:45, 15:1 to 1:40, 15:1 to 1:35, 15:1 to 1:30, 15:1 to 1:25, 15:1 to 1:20, 15:1 to 1:10, 15:1 to 1:5, 15:1 to 1:4, 15:1 to 1:3, 15:1 to 1:2, 10:1 to 1:10, 10:1 to 1:95, 10:1 to 1:90, 10:1 to 1:85, 10:1 to 1:80, 10:1 to 1:75, 10:1 to 1:70, 10:1 to 1:65, 10:1 to 1:60, 10:1 to 1:55, 10:1 to 1:50, 10:1 to 1:45, 10:1 to 1:40, 10:1 to 1:35, 10:1 to 1:30, 10:1 to 1:25, 10:1 to 1:20, 10:1 to 1:15, 10:1 to 1:5, 10:1 to 1:4, 10:1 to 1:3, 10:1 to 1:2, 5:1 to 1:5, 5:1 to 1:95, 5:1 to 1:90, 5:1 to 1:85, 5:1 to 1:80, 5:1 to 1:75, 5:1 to 1:70, 5:1 to 1:65, 5:1 to 1:60, 5:1 to 1:55, 5:1 to 1:50, 5:1 to 1:45, 5:1 to 1:40, 5:1 to 1:35, 5:1 to 1:30, 5:1 to 1:25, 5:1 to 1:20, 5:1 to 1:15, 5:1 to 1:10, 5:1 to 1:4, 5:1 to 1:3, 5:1 to 1:2, 4:1 to 1:4, 4:1 to 1:95, 4:1 to 1:90, 4:1 to 1:85, 4:1 to 1:80, 4:1 to 1:75, 4:1 to 1:70, 4:1 to 1:65, 4:1 to 1:60, 4:1 to 1:55, 4:1 to 1:50, 4:1 to 1:45, 4:1 to 1:40, 4:1 to 1:35, 4:1 to 1:30, 4:1 to 1:25, 4:1 to 1:20, 4:1 to 1:15, 4:1 to 1:10, 4:1 to 1:5, 4:1 to 1:3, 4:1 to 1:2, 3:1 to 1:3, 3:1 to 1:95, 3:1 to 1:90, 3:1 to 1:85, 3:1 to 1:80, 3:1 to 1:75, 3:1 to 1:70, 3:1 to 1:65, 3:1 to 1:60, 3:1 to 1:55, 3:1 to 1:50, 3:1 to 1:45, 3:1 to 1:40, 3:1 to 1:35, 3:1 to 1:30, 3:1 to 1:25, 3:1 to 1:20, 3:1 to 1:15, 3:1 to 1:10, 3:1 to 1:5, 3:1 to 1:4, 3:1 to 1:2, 2:1 to 1:2, 2:1 to 1:95, 2:1 to 1:90, 2:1 to 1:85, 2:1 to 1:80, 2:1 to 1:75, 2:1 to 1:70, 2:1 to 1:65, 2:1 to 1:60, 2:1 to 1:55, 2:1 to 1:50, 2:1 to 1:45, 2:1 to 1:40, 2:1 to 1:35, 2:1 to 1:30, 2:1 to 1:25, 2:1 to 1:20, 2:1 to 1:15, 2:1 to 1:10, 2:1 to 1:5, 2:1 to 1:4, 2:1 to 1:3.

The composition of the present invention may further comprise at least one other different fungicide active ingredient (c).

Examples of suitable fungicide mixing partners may be selected in the following lists:

c1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

c2) a compound capable to inhibit the mitosis and cell division like benomyl, carbendazim, diethofencarb, ethaboxam, fuberidazole, pencycuron, thiabendazole thiophanate-methyl, zoxamide;

c3) a compound capable to inhibit the respiration for example as CI-respiration inhibitor like diflumetorim;
as CII-respiration inhibitor like boscalid, carboxin, fenfuram, flutolanil, furametpyr, furmecyclox, mepronil, oxycarboxine, penthiopyrad, thifluzamide;
as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

c4) a compound capable of to act as an uncoupler like dinocap, fluazinam, meptyldinocap;

c5) a compound capable to inhibit ATP production like fentin acetate, fentin chloride, fentin hydroxide, silthiofam;

c6) a compound capable to inhibit AA and protein biosynthesis like andoprim, blasticidin-S, cyprodinil, kasugamycin, kasugamycin hydrochloride hydrate, mepanipyrim, pyrimethanil;

c7) a compound capable to inhibit the signal transduction like fenpiclonil, fludioxonil, quinoxyfen;

c8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

c9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

c10) a compound capable to inhibit cell wall synthesis like benthiavalicarb, bialaphos, dimethomorph, flumorph, iprovalicarb, mandipropamid, polyoxins, polyoxorim, validamycin A;

c11) a compound capable to inhibit melanine biosynthesis like carpropamid, diclocymet, fenoxanil, phthalide, pyroquilon, tricyclazole;

c12) a compound capable to induce a host defence like acibenzolar-5-methyl, probenazole, tiadinil;

c13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations including calcium polysulphide, thiram, tolylfluanid, zineb, ziram;

c14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-[2-(1,3-dimethylbutyl)phenyl]-5-fluoro-1,3-dimethyl-1H-pyrazole-4-carboxamide, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chloro-phenyl)prop-2-yn-1-yl]oxy}-3-methoxyphenyl)ethyl]-N<-(methylsulfonyl)valinamide, N-{(Z)-[(Cyclopropylmethoxy)imino][6-(difluoromethoxy)-2,3-difluorophenyl]methyl}-2-phenyl-acetamide, N-{2-[1,1'-bi(cyclopropyl)-2-yl]phenyl}-3-(difluoromethyl)-, 1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, 0-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, tecloftalam, tecnazene, triazoxide, trichlamide, valiphenal, zarilamid.

Preferably, fungicidal active ingredient (c) is selected from 5-fluoro-1,3-dimethyl-N-[2-(1,3-dimethyl)-but-2-ol-yl]-1H-pyrazole-4-carboxamide, N-[2-(1,3-dimethylbutyl)phenyl]-5-fluoro-1,3-dimethyl-1H-pyrazole-4-carboxamide, benalaxyl, benalaxyl-M, benthiavalicarb, carboxin, chlorothalonil, cyazofamid, cymoxanil, dimetomorph, fluazinam, fludioxonil, fluquinconazole, fluoxastrobin, flutriafol, fosetyl-aluminium, hexaconazole, hymexazole, ipconazole, mancozeb, mandipropamid, maneb, mefenoxam, metiram, metalaxyl, metalaxyl-M, peconazole, penthiopyrad, phosphorous acid, propamocarb.HCl, propineb, prothioconazole, tebuconazole, thiram, triadimenol, trifloxystrobin and triticonazole.

Where the third active ingredient (c) as defined above is present in the composition, this compound may be present in an amount of (a):(b):(c) weight ratio of from 1:0.001:0.001 to 1:1000:1000; the ratios of compound (a) and compound (c) varying independently from each other. Preferably, the (a):(b):(c) weight ratio may be of from 1:0.01:0.01 to 1:100:100. More preferably, the (a):(b):(c) weight ratio may be of from 1:0.05:0.05 to 1:80:80.

Following compositions may be cited to illustrate in a non-limited manner the present invention: fenamidone with N-[2-(1,3-dimethylbutyl)phenyl]-5-fluoro-1,3-dimethyl-1H-pyrazole-4-carboxamide, and clothianidin, fenamidone with benalaxyl and clothianidin, fenamidone with benalaxyl-M and clothianidin, fenamidone with benthiavalicarb and clothianidin, fenamidone with carboxin and clothianidin, fenamidone with chlorothalonil and clothianidin, fenamidone with cyazofamid and clothianidin, fenamidone with cymoxanil and clothianidin, fenamidone with dimetomorph and clothianidin, fenamidone with fluazinam and clothianidin, fenamidone with fludioxonil and clothianidin, fenamidone with fluquinconazole and clothianidin, fenamidone with fluoxastrobin and clothianidin, fenamidone with flutriafol and clothianidin, fenamidone with fosetyl-aluminium and clothianidin, fenamidone with hexaconazole and clothianidin, fenamidone with hymexazole and clothianidin, fenamidone with ipconazole and clothianidin, fenamidone with mancozeb and clothianidin, fenamidone with mandipropamid and clothianidin, fenamidone with maneb and clothianidin, fenamidone with mefenoxam and clothianidin, fenamidone with metiram and clothianidin, fenamidone with metalaxyl and clothianidin, fenamidone with metalaxyl-M and clothianidin, fenamidone with peconazole and clothianidin, fenamidone with penthiopyrad and clothianidin, fenamidone with phosphorous acid and clothianidin, fenamidone with propamocarb.HCl and clothianidin, fenamidone with propineb and clothianidin, fenamidone with prothioconazole and clothianidin, fenamidone with tebuconazole and clothianidin, fenamidone with thiram and clothianidin, fenamidone with triadimenol and clothianidin, fenamidone with trifloxystrobin and clothianidin, fenamidone with triticonazole and clothianidin, fenamidone with N-[2-(1,3-dimethylbutyl)phenyl]-5-fluoro-1,3-dimethyl-1H-pyrazole-4-carboxamide and imidacloprid, fenamidone with benalaxyl and imidacloprid, fenamidone with benalaxyl-M and imidacloprid, fenamidone with benthiavalicarb and imidacloprid, fenamidone with carboxin and imidacloprid, fenamidone with chlorothalonil and imidacloprid, fenamidone with cyazofamid and imidacloprid, fenamidone with cymoxanil and imidacloprid, fenamidone with dimetomorph and imidacloprid, fenamidone with fluazinam and imidacloprid, fenamidone with fludioxonil and imidacloprid, fenamidone with fluquinconazole and imidacloprid, fenamidone with fluoxastrobin and imidacloprid, fenamidone with flutriafol and imidacloprid, fenamidone with fosetyl-aluminium and imidacloprid, fenamidone with hexaconazole and imidacloprid, fenamidone with hymexazole and imidacloprid, fenamidone with ipconazole and imidacloprid, fenamidone with mancozeb and imidacloprid, fenamidone with mandipropamid and imidacloprid, fenamidone with maneb and imidacloprid, fenamidone with mefenoxam and imidacloprid, fenamidone with metiram and imidacloprid, fenamidone with metalaxyl and imidacloprid, fenamidone with metalaxyl-M and imidacloprid, fenamidone with peconazole and imidacloprid, fenamidone with penthiopyrad and imidacloprid, fenamidone with phosphorous acid and imidacloprid, fenamidone with propamocarb.HCl and imidacloprid, fenamidone with propineb and imidacloprid, fenamidone with prothioconazole and imidacloprid, fenamidone with tebuconazole and imidacloprid, fenamidone with thiram and imidacloprid, fenamidone with triadimenol and imidacloprid, fenamidone with trifloxystrobin and imidacloprid, fenamidone with triticonazole and imidacloprid, fenamidone with 5-fluoro-1,3-dimethyl-N-[2-(1,3-dimethyl)-but-2-ol-yl]-1H-pyrazole-4-carboxamide and thiametoxam, fenamidone with benalaxyl and thiametoxam, fenamidone with benalaxyl-M and thiametoxam, fenamidone with benthiavalicarb and thiametoxam, fenamidone with carboxin and thiametoxam, fenamidone with chlorothalonil and thiametoxam, fenamidone with cyazofamid and thiametoxam, fenamidone with cymoxanil and thiametoxam, fenamidone with dimetomorph and thiametoxam, fenamidone with fluazinam and thiametoxam, fenamidone with fludioxonil and thiametoxam, fenamidone with fluquinconazole and thiametoxam, fenamidone with fluoxastrobin and thiametoxam, fenamidone with flutriafol and thiametoxam, fenamidone with fosetyl-aluminium and thiametoxam, fenamidone with hexaconazole and thiametoxam, fenamidone with hymexazole and thiametoxam, fenamidone with ipconazole and thiametoxam, fenamidone with mancozeb and thiametoxam, fenamidone with mandipropamid and thiametoxam, fenamidone with maneb and thiametoxam, fenamidone with mefenoxam and thiametoxam, fenamidone with metiram and thiametoxam, fenamidone with metalaxyl and thiametoxam, fenamidone with metalaxyl-M and thiametoxam, fenamidone with peconazole and thiametoxam, fenamidone with penthiopyrad and thiametoxam, fenamidone with phosphorous acid and thiametoxam, fenamidone with propamocarb.HCl and thiametoxam, fenamidone with propineb and thiametoxam, fenamidone with prothioconazole and thiametoxam, fenamidone with tebuconazole and thiametoxam, fenamidone with thiram and thiametoxam, fenamidone with triadimenol and thiametoxam, fenamidone with trifloxystrobin and thiametoxam and fenamidone with triticonazole and thiametoxam.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The pesticidal compositions of the present invention can be used to curatively or preventively control phytopathogenic fungi of crops but also to curatively or preventively control insects.

Thus, according to a further aspect of the present invention, there is provided a method for preventively or curatively controlling phytopathogenic fungi of crops but also to curatively or preventively control insects characterised in that an effective and non-phytotoxic amount of a composition as hereinbefore defined is applied via seed treatment, foliar application, stem application or drench/drip application (chemigation) to the seed, the plant and/or to the fruit of the plant or to soil and/or to inert substrate (e.g. inorganic substrates (e.g. sand, rockwool, glasswool, expanded minerals (e.g. perlite, vermiculite, zeolite, expanded clay)), Pumice, Pyroclastic materials/tuff, synthetic organic substrates (e.g. Polyurethane), organic substrates (e.g. peat, composts, tree waste products (e.g. coir, wood fibre/chips, tree bark)) and/or to a liquid substrate (e.g. floating hydroponic systems, Nutrient Film Technique, Aeroponics) in which the plant is growing or in which it is desired to grow.

The expression "effective and non-phytotoxic amount" means an amount of composition according to the invention which is sufficient to control or destroy the pests and/or diseases present or liable to appear on the crops, and which does not entail any appreciable symptom of phytotoxicity for the said crops. Such an amount can vary within a wide range depending on the pests and diseases to be combated or controlled, the type of crop, the climatic conditions and the compounds included in the composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as bamase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. Nos. 5,605,011, 5,378,824, 5,141,870, and 5,013,659. The production of sulfonylurea-tolerant plants and imidazolinone-tolerant plants is described in U.S. Pat. No. 5,605,011; 5,013,659; 5,141,870; 5,767,361; 5,731,180; 5,304,732; 4,761,373; 5,331,107; 5,928,937; and 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.

b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. Nos. 5,824,790, 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. Nos. 6,284,479, 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes as described in WO 1998/000549
b) Plants, such as cotton plants, containing an altered form of rsw2 or rsw3 homologous nucleic acids as described in WO2004/053219
c) Plants, such as cotton plants, with increased expression of sucrose phosphate synthase as described in WO 2001/017333
d) Plants, such as cotton plants, with increased expression of sucrose synthase as described in WO02/45485
e) Plants, such as cotton plants, wherein the timing of the plasmodesmatal gating at the basis of the fiber cell is altered, e.g. through downregulation of fiberselective β 1,3-glucanase as described in WO2005/017157
f) Plants, such as cotton plants, having fibers with altered reactivity, e.g. through the expression of N-acteylglucosaminetransferase gene including nodC and chitin-synthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:
a) Plants, such as oilseed rape plants, producing oil having a high oleic acid content as described e.g. in U.S. Pat. Nos. 5,969,169, 5,840,946 or 6,323,392 or 6,063,947
b) Plants such as oilseed rape plants, producing oil having a low linolenic acid content as described in U.S. Pat. Nos. 6,270,828, 6,169,190 or 5,965,755
c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

Among the diseases of plants or crops that can be controlled by the method according to the present invention, mention may be made of:

Powdery mildew diseases such as:
*Blumeria* diseases, caused for example by *Blumeria graminis*;
*Leveillula* diseases, caused for example by *Leveillula taurica*
*Podosphaera* diseases, caused for example by *Podosphaera leucotricha*;
*Sphaerotheca* diseases, caused for example by *Sphaerotheca fuliginea* or *Sphaerotheca pannosa*;
*Uncinula* diseases, caused for example by *Uncinula necator*;
Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;
Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;

Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporum cucumerinum*;
Cochliobolus diseases, caused for example by *Cochliobolus sativus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Diplocarpon diseases, caused for example by *Diplocarpon rosae*
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella arachidicola*; *Mycosphaerella fijiensis*;
Phaeosphaeria diseases, caused for example by *Phaeosphaeria nodorum*;
Pyrenophora diseases, caused for example by *Pyrenophora teres*;
Ramularia diseases, caused for example by *Ramularia collocygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incarnata*;
Venturia diseases, caused for example by *Venturia inaequalis*;
Root and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminis*;
Rhizoctonia diseases, caused for example by *Rhizoctonia solani*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.;
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;
Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;
Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Sclerotinia diseases, caused for example by *Sclerotinia sclerotiorum*;
Verticilium diseases, caused for example by *Verticilium alboatrum*;
Seed and soilborne decay, mould, wilt, rot and damping-off diseases:
Fusarium diseases, caused for example by *Fusarium culmorum*;
Phytophthora diseases, caused for example by *Phytophthora cactorum*;
Pythium diseases, caused for example by *Pythium ultimum*;
Rhizoctonia diseases, caused for example by *Rhizoctonia solani*;
Sclerotium diseases, caused for example by *Sclerotium rolfsii*;
Microdochium diseases, caused for example by *Microdochium nivale*;
Canker, broom and dieback diseases such as:
Nectria diseases, caused for example by *Nectria galligena*;
Blight diseases such as:
Monilinia diseases, caused for example by *Monilinia laxa*;
Leaf blister or leaf curl diseases such as:
Taphrina diseases, caused for example by *Taphrina deformans*;
Decline diseases of wooden plants such as:
Esca diseases, caused for example by *Phaemoniella clamydospora*;
Diseases of flowers and Seeds such as:
Botrytis diseases, caused for example by *Botrytis cinerea*;
Diseases of tubers such as:
Rhizoctonia diseases, caused for example by *Rhizoctonia solani*;
Helminthosporium diseases, caused for example by *Helminthosporium solani*.

Furthermore the treatments according to the invention can be able to reduce the contents of mycotoxins in the harvested crops and therefore in foods and animal feed stuff made therefrom.

Especially but not exclusively the following mycotoxins can be specified:
Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalcaloides und Aflatoxines, which are caused for example by the following fungal diseases: *Fusarium* spec., like *Fusarium acuminatum, F. avenaceum, F. crookwellense, F. culmorum, F.*

*graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The composition according to the present invention is well tolerated by plants, have favourable homeotherm toxicity and are environmentally friendly; it is suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. It is preferably used as crop protection agents. It is active against normally sensitive and resistant species and against all or some stages of development. Among the animal pests that can also be controlled by the method according to the present invention, mention may be made of:

Pest from the order of the Isopoda, for example *Oniscus asellus, Armadillidium vulgare* and *Porcellio scaber;*

Pest from the order of the Diplopoda, for example *Blaniulus guttulatus;*

Pest from the order of the Chilopoda, for example *Geophilus carpophagus* and *Scutigera* spp.;

Pest from the order of the Symphyla, for example *Scutigerella immaculate;*

Pest from the order of the Thysanura, for example *Lepisma saccharina;*

Pest from the order of the Collembola, for example *Onychiurus armatus;*

Pest from the order of the Orthoptera, for example *Acheta domesticus, Gryllotalpa* spp., *Locusta migratoria migratorioides, Melanoplus* spp. and *Schistocerca gregaria;*

Pest from the order of the Blattaria, for example *Blatta orientalis, Periplaneta americana, Leucophaea maderae* and *Blattella germanica;*

Pest from the order of the Dermaptera, for example *Forficula auricularia;*

Pest from the order of the Isoptera, for example *Reticulitermes* spp.;

Pest from the order of the Phthiraptera, for example *Pediculus humanus corporis, Haematopinus* spp., *Linognathus* spp., *Trichodectes* spp., *Damalinia* spp.;

Pest from the order of the Thysanoptera, for example *Hercinothrips femoralis, Thrips tabaci, Thrips palmi, Frankliniella accidentalis;*

Pest from the order of the Heteroptera, for example *Eurygaster* spp., *Dysdercus intermedius, Piesma quadrata, Cimex lectularius, Rhodniusprolixus* and *Triatoma* spp.;

Pest from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

Pest from the order of the Lepidoptera, for example *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae;*

Pest from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus;*

Pest from the order of the Hymenoptera, for example *Diprion* spp., *Hoplocampa* spp., *Lasius* spp., *Monomorium pharaonis* and *Vespa* spp.;

Pest from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.;

Pest from the order of the Siphonaptera, for example *Xenopsylla cheopis* and *Ceratophyllus* spp.;

Pest from the class of the Arachnida, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.;

The plant-parasitic nematodes such as *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The composition according to the present invention may also be used against pests and diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. If a drench/drip application is possible, the dose can be lower, especially in artificial substrates like rockwool or perlite. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

BIOLOGICAL EXAMPLES

Formula for the Efficacy of the Combination of Two Compounds

The expected efficacy of a given combination of two compounds is calculated as follows (see Colby, S. R., "Calculating Synergistic and antagonistic Responses of Herbicide Combinations", Weeds 15, pp. 20-22, 1967):

If

X is the efficacy expressed in % mortality of the untreated control for test compound A at a concentration of m ppm respectively m g/ha, Y is the efficacy expressed in % mortality of the untreated control for test compound B at a concentration of n ppm respectively n g/ha, E is the efficacy expressed in % mortality of the untreated control using the mixture of A and B at m and n ppm respectively m and n g/ha, $$E = X + Y - \frac{X \times Y}{100}$$

If the observed insecticidal efficacy of the combination is higher than the one calculated as "E", then the combination of the two compounds is more than additive, i.e., there is a synergistic effect.

Example A

*Plutella xylostella*—Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the diamond back moth (*Plutella xylostella*) as long as the leaves are still moist.

After the specified period of time, the mortality in % is determined. 100% means that all the caterpillars have been killed; 0% means that none of the caterpillars have been killed.

According to the present application in this test e.g. the following combinations of Table A show a synergistic effect in comparison to the single compounds:

TABLE A plant damaging insects
*Plutella xylostella* - test

| Active Ingredient | Concentration in ppm | | |
|---|---|---|---|
| | | Efficacy in % after $4^d$ | |
| Fenamidone | 500 | 75 | |
| | 200 | 35 | |
| Imidacloprid | 20 | 5 | |
| Thiamethoxam | 4 | 0 | |
| | | obs.* | cal.** |
| Fenamidone + Imidacloprid (25:1) according to the invention | 500 + 20 | 100 | 76.25 |
| Fenamidone + Thiamethoxam (50:1) according to the invention | 200 + 4 | 100 | 35 |
| | | Efficacy in % after $4^d$ | |
| Fenamidone | 200 | 65 | |
| Clothianidin | 4 | 0 | |
| | | obs.* | cal.** |
| Fenamidone + Clothianidin (50:1) according to the invention | 200 + 4 | 100 | 65 |

*obs. = observed insecticidal efficacy
**cal. = efficacy calculated with Colby-formula Example B

*Spodoptera exigua*—Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the beet army worm (*Spodoptera exigua*) as long as the leaves are still moist.

After the specified period of time, the mortality in % is determined. 100% means that all the caterpillars have been killed; 0% means that none of the caterpillars have been killed.

According to the present application in this test e.g. the following combinations of table B show a synergistic effect in comparison to the single compounds:

TABLE B plant damaging insects
*Spodoptera exigua* - test

| Active Ingredient | Concentration in ppm | Efficacy in % after $3^d$ | |
|---|---|---|---|
| Fenamidone | 100 | 0 | |
| Thiacloprid | 100 | 10 | |
| | | obs.* | cal.** |
| Fenamidone + Thiacloprid (1:1) erfindungsgemäß | 100 + 100 | 35 | 10 |
| Fenamidone | 200 | 0 | |
| Imidacloprid | 20 | 0 | |
| | | obs.* | cal.** |
| Fenamidone + Imidacloprid (10:1) according to the invention | 200 + 20 | 20 | 0 |

*obs. = observed insecticidal efficacy
**cal. = efficacy calculated with Colby-formula Example C

*Spodoptera frugiperda*—Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the fall army worm (*Spodoptera frugiperda*) as long as the leaves are still moist.

After the specified period of time, the mortality in % is determined. 100% means that all the caterpillars have been killed; 0% means that none of the caterpillars have been killed.

According to the present application in this test e.g. the following combinations of Table C show a synergistic effect in comparison to the single compounds:

TABLE C plant damaging insects
*Spodoptera frugiperda* - test

| Active Ingredient | Concentration in ppm | Efficacy in % after $4^d$ | |
|---|---|---|---|
| Fenamidone | 200 | 0 | |
| Clothianidin | 4 | 0 | |
| | | obs.* | cal.** |
| Fenamidone + Clothianidin (50:1) according to the invention | 200 + 4 | 75 | 0 |

*obs. = observed insecticidal efficacy
**cal. = efficacy calculated with Colby-form

The invention claimed is:

1. A composition comprising:
   a) fenamidone; and
   b) an insecticide compound;
   in a (a)/(b) weight ratio of from 1/1000 to 1000/1;
   wherein said insecticide compound is a chloride channel activator selected from the group consisting of abamectin, avermectin, emamectin, emamectin-benzoate, ivermectin, lepimectin, milbemectin, and milbemycin.

2. A composition according to claim 1 further comprising a fungicide compound (c).

3. A composition according to claim 2, wherein compounds (a), (b) and (c) are present in an amount of (a):(b):(c) weight ratio of from 1:0.001:0.001 to 1:1000 :1000.

4. A composition according to claim 2, wherein the fungicide compound (c) is selected from the group consisting of benalaxyl, benalaxyl-M, benthiavalicarb, carboxin, chlorothalonil, cyazofamid, cymoxanil, dimetomorph, fluazinam, fludioxonil, fluquinconazole, fluoxastrobin, flutriafol, fosetyl-aluminium, hexaconazole, hymexazole, ipconazole, mancozeb, mandipropamid, maneb, mefenoxam, metiram, metalaxyl, peconazole, penthiopyrad, phosphorous acid, propamocarb.HCl, propineb, prothioconazole, tebuconazole, thiram, triadimenol, trifloxystrobin and triticonazole.

5. A method for controlling phytopathogenic fungi of crops and/or insects comprising applying an effective and non-phytotoxic amount of a composition according to claim 2 via seed treatment, foliar application, stem application and/or drench/drip application to a seed, a plant and/or to a fruit of a plant and/or to soil and/or to inert substrate, Pumice, a Pyroclastic material, a synthetic organic substrate, an organic substrate and/or to a liquid substrate in which a plant is growing or in which a plant is desired to grow.

6. A composition according to claim 2, wherein said fungicide compound (c) is benalaxyl.

7. A composition according to claim 2, wherein compounds (a), (b), and (c) are present in an amount of (a):(b):(c) weight ratio of from 1:0.01:0.01 to 1:100:100.

8. A composition according to claim 2, wherein compounds (a), (b), and (c) are present in an amount of (a):(b):(c) weight ratio of from 1:0.05:0.05 to 1:80:80.

9. A composition according to claim 1, further comprising an agriculturally acceptable support, carrier, filler and/or surfactant.

10. A method for controlling phytopathogenic fungi of crops and/or insects comprising applying an effective and non-phytotoxic amount of a composition according to claim 1 via seed treatment, foliar application, stem application and/or drench/drip application to seed, a plant and/or to fruit of a plant and/or to soil and/or to inert substrate, Pumice, a Pyroclastic material, a synthetic organic substrate, an organic substrate and/or to a liquid substrate in which a plant is growing and/or in which a plant is desired to grow.

11. A composition according to claim 1, wherein said insecticidal compound (b) is abamectin.

12. A composition according to claim 1, wherein compounds (a) and (b) are present in a weight ratio of from 1/125 to 125/1.

13. A composition according to claim 1, wherein compounds (a) and (b) are present in a weight ratio of from 1/25 to 25/1.

14. A composition according to claim 1, wherein said insecticidal compound (b) is avermectin.

15. A composition according to claim 1, wherein said insecticidal compound (b) is emamectin.

16. A composition according to claim 1, wherein said insecticidal compound (b) is emamectin-benzoate.

17. A composition according to claim 1, wherein said insecticidal compound (b) is ivermectin.

18. A composition according to claim 1, wherein said insecticidal compound (b) is lepimectin.

19. A composition according to claim 1, wherein said insecticidal compound (b) is milbemectin.

20. A composition according to claim 1, wherein said insecticidal compound (b) is milbemycin.

* * * * *